United States Patent
Matsubara et al.

(10) Patent No.: US 10,504,223 B2
(45) Date of Patent: *Dec. 10, 2019

(54) CELL IMAGE EVALUATION DEVICE, METHOD, AND PROGRAM

(71) Applicant: FUJIFILM Corporation, Tokyo (JP)

(72) Inventors: Kenta Matsubara, Ashigarakami-gun (JP); Tsuyoshi Matsumoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 61 days.

This patent is subject to a terminal disclaimer.

(21) Appl. No.: 15/046,592

(22) Filed: Feb. 18, 2016

(65) Prior Publication Data

US 2016/0163049 A1 Jun. 9, 2016

Related U.S. Application Data

(63) Continuation of application No. PCT/JP2014/004206, filed on Aug. 18, 2014.

(30) Foreign Application Priority Data

Aug. 22, 2013 (JP) .................................. 2013-172380
Mar. 5, 2014 (JP) .................................. 2014-043255

(51) Int. Cl.
*G06T 7/00* (2017.01)
*G06K 9/62* (2006.01)
(Continued)

(52) U.S. Cl.
CPC ........... *G06T 7/0012* (2013.01); *C12M 41/36* (2013.01); *C12M 41/46* (2013.01); *G02B 21/365* (2013.01);
(Continued)

(58) Field of Classification Search
None
See application file for complete search history.

(56) References Cited

U.S. PATENT DOCUMENTS 7,907,769 B2 * 3/2011 Sammak ............ G06K 9/00127
382/133
8,189,900 B2 * 5/2012 Sammak ............ G06K 9/00127
382/133
(Continued)

FOREIGN PATENT DOCUMENTS

JP 2011-229410 A 11/2011
JP 2011-229409 A 11/2011
(Continued)

OTHER PUBLICATIONS

English translation of JP2007072707 dated Mar. 2007; Masaki et al.*

(Continued)

*Primary Examiner* — Nancy Bitar
(74) *Attorney, Agent, or Firm* — Sughrue Mion, PLLC

(57) ABSTRACT

A cell image evaluation device includes an image acquisition unit that acquires a captured image of a cell, a cell evaluation unit that evaluates the cell image, and a maturity information acquisition unit that acquires information related to maturity of the cell. The cell evaluation unit determines a method for evaluating the cell image on the basis of the information related to the maturity.

11 Claims, 10 Drawing Sheets

(51) Int. Cl.
  *G06K 9/00* (2006.01)
  *C12M 1/34* (2006.01)
  *G02B 21/36* (2006.01)
  *G01N 21/41* (2006.01)
  *G02B 21/14* (2006.01)

(52) U.S. Cl.
  CPC ......... *G06K 9/0014* (2013.01); *G06K 9/6227* (2013.01); *G01N 2021/4173* (2013.01); *G02B 21/14* (2013.01); *G06T 2207/10056* (2013.01); *G06T 2207/30024* (2013.01)

(56) References Cited

U.S. PATENT DOCUMENTS

| | | | | |
|---|---|---|---|---|
| 9,600,874 | B2* | 3/2017 | Fujimoto | G06T 7/0012 |
| 9,723,989 | B2* | 8/2017 | Nolte | G02B 21/14 |
| 2009/0130703 | A1* | 5/2009 | Wagner | C40B 30/04 |
| | | | | 435/29 |
| 2012/0122143 | A1 | 5/2012 | Mimura et al. | |
| 2014/0248648 | A1* | 9/2014 | Chirila | G01N 33/5091 |
| | | | | 435/29 |
| 2016/0232682 | A1* | 8/2016 | Nakagawa | C12M 41/36 |
| 2017/0061618 | A1* | 3/2017 | Matsubara | C12Q 1/02 |

FOREIGN PATENT DOCUMENTS

| | | |
|---|---|---|
| JP | 4852890 B2 | 1/2012 |
| JP | 2012-95627 A | 5/2012 |
| JP | 2011229409 * | 11/2017 |
| WO | 2011/013319 A1 | 2/2011 |
| WO | 2012/115153 A1 | 8/2012 |

OTHER PUBLICATIONS

JP 2007072707 A "Maturation Value Assessment Method for System or Service, Assessment Sheet and Service Maturation Value Assessment System" Masaki et al Mar. 22, 2007.*
High Content Analysis of Human Embryonic Stem Cell Growth and Differentiation 205 Paul J. Sammak, Vivek Abraham, Richik Ghosh, Jeff Haskins, Esther Jane, Patti Petrosko, Teresa M. Erb, Tia N. Kinney, Feb. 2007.*
BMC Cell Biology Automated measurement of cell motility and proliferationAlfred Bahnson et al. Apr. 14, 2005 (Year: 2005).*
Ryouta Soukejima et al. "Analysis aiding for epigenetic mechanism by image processing", ITE Technical Report, 2010, pp. 97-100, vol. 34, No. 10.
International Search Report for PCT/JP2014/004206 dated Jan. 6, 2015.
Written Opinion for PCT/JP2014/004206 dated Jan. 6, 2015.
Communication dated Aug. 9, 2016, from the Japanese Patent Office in counterpart Japanese application No. 2014-043255.

* cited by examiner

FIG. 2

| TIME ELAPSED (MATURITY) | INITIAL STAGE OF SEEDING | STAGE AFTER LAPSE OF A FEW DAYS FROM SEEDING | STAGE AFTER LAPSE OF A WEEK FROM SEEDING |
|---|---|---|---|
| COLONY SEEDING | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON UNIFORMITY OF STEM CELL AND SHAPE OF COLONY<br><br>WEIGHT    UNIFORMITY: LARGE<br>         SHAPE OF COLONY: SMALL | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON UNIFORMITY OF STEM CELL AND SHAPE OF COLONY<br><br>WEIGHT    UNIFORMITY: LARGE<br>         SHAPE OF COLONY: MEDIUM | MEASUREMENT BY DIFFERENTIAL INTERFERENCE MICROSCOPE<br><br>SEPARATION OF DIFFERENT TYPES OF CELLS<br><br>EXTRACTION OF COLONY<br><br>DETERMINATION BASED ON SHAPE OF COLONY, UNIFORMITY OF BRIGHTNESS, AND UNIFORMITY OF THICKNESS<br><br>WEIGHT    CIRCULARITY: SMALL<br>APPROXIMATION OF OUTWARD SHAPE OF CELL TO COMBINATION PATTERN OF A PLURALITY OF CIRCLES: LARGE<br>INTERNAL DEFECT: LARGE<br>UNIFORMITY OF BRIGHTNESS: LARGE<br>UNIFORMITY OF THICKNESS: LARGE |
| SINGLE STEM CELL SEEDING | MEASUREMENT BY PHASE CONTRAST MICROSCOPE<br><br>DETERMINATION BASED ON UNIFORMITY OF STEM CELL AND SHAPE OF COLONY<br><br>WEIGHT    UNIFORMITY: LARGE<br>         SHAPE OF COLONY: SMALL | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON UNIFORMITY OF STEM CELL AND SHAPE OF COLONY<br><br>WEIGHT    UNIFORMITY: LARGE<br>         SHAPE OF COLONY: MEDIUM | MEASUREMENT BY DIFFERENTIAL INTERFERENCE MICROSCOPE<br><br>SEPARATION OF DIFFERENT TYPES OF CELLS<br><br>EXTRACTION OF COLONY<br><br>DETERMINATION BASED ON SHAPE OF COLONY, UNIFORMITY OF BRIGHTNESS, AND UNIFORMITY OF THICKNESS<br><br>WEIGHT    CIRCULARITY: SMALL<br>APPROXIMATION OF OUTWARD SHAPE OF CELL TO COMBINATION PATTERN OF A PLURALITY OF CIRCLES: LARGE<br>INTERNAL DEFECT: LARGE<br>UNIFORMITY OF BRIGHTNESS: LARGE<br>UNIFORMITY OF THICKNESS: LARGE |

THERE ARE DIFFERENT TYPES OF CELLS

FIG. 3

| TIME ELAPSED (MATURITY) | | INITIAL STAGE OF SEEDING | STAGE AFTER LAPSE OF A FEW DAYS FROM SEEDING | STAGE AFTER LAPSE OF A WEEK FROM SEEDING |
|---|---|---|---|---|
| THERE ARE NO DIFFERENT TYPES OF CELLS | COLONY SEEDING | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON UNIFORMITY OF STEM CELL AND SHAPE OF COLONY<br><br>WEIGHT  UNIFORMITY :LARGE<br>       SHAPE OF COLONY :SMALL | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON UNIFORMITY OF STEM CELL AND SHAPE OF COLONY<br><br>WEIGHT  UNIFORMITY :LARGE<br>       SHAPE OF COLONY :MEDIUM | MEASUREMENT BY DIFFERENTIAL INTERFERENCE MICROSCOPE<br><br>SEPARATION OF DIFFERENT TYPES OF CELLS<br><br>EXTRACTION OF COLONY<br><br>DETERMINATION BASED ON SHAPE OF COLONY, UNIFORMITY OF BRIGHTNESS, AND UNIFORMITY OF THICKNESS<br><br>WEIGHT  CIRCULARITY: SMALL<br>APPROXIMATION OF OUTWARD SHAPE OF CELL TO COMBINATION PATTERN OF A PLURALITY OF CIRCLES: LARGE<br>INTERNAL DEFECT: LARGE<br>UNIFORMITY OF BRIGHTNESS: LARGE<br>UNIFORMITY OF THICKNESS: LARGE |
| | SINGLE STEM CELL SEEDING | MEASUREMENT BY PHASE CONTRAST MICROSCOPE<br><br>DETERMINATION BASED ON UNIFORMITY OF STEM CELL AND SHAPE OF COLONY<br><br>WEIGHT  UNIFORMITY :LARGE<br>       SHAPE OF COLONY :SMALL | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON UNIFORMITY OF STEM CELL AND SHAPE OF COLONY<br><br>WEIGHT  UNIFORMITY :LARGE<br>       SHAPE OF COLONY :MEDIUM | MEASUREMENT BY PHASE CONTRAST MICROSCOPE<br><br>SEPARATION OF DIFFERENT TYPES OF CELLS<br><br>EXTRACTION OF COLONY<br><br>DETERMINATION BASED ON SHAPE OF COLONY<br><br>WEIGHT  CIRCULARITY: SMALL<br>APPROXIMATION OF OUTWARD SHAPE OF CELL TO COMBINATION PATTERN OF A PLURALITY OF CIRCLES: LARGE<br>INTERNAL DEFECT: LARGE |

FIG. 4

| TIME ELAPSED (MATURITY) | INITIAL STAGE OF SEEDING | STAGE AFTER LAPSE OF A FEW DAYS FROM SEEDING | STAGE AFTER LAPSE OF A WEEK FROM SEEDING |
|---|---|---|---|
| | MEASUREMENT BY PHASE CONTRAST MICROSCOPE | MEASUREMENT BY PHASE CONTRAST MICROSCOPE | MEASUREMENT BY PHASE CONTRAST MICROSCOPE |
| | | SEPARATION OF DIFFERENT TYPES OF CELLS | SEPARATION OF DIFFERENT TYPES OF CELLS |
| | | EXTRACTION OF COLONY | EXTRACTION OF COLONY |
| | DETERMINATION BASED ON UNIFORMITY OF STEM CELL AND SHAPE OF COLONY | DETERMINATION BASED ON UNIFORMITY OF STEM CELL AND SHAPE OF COLONY | DETERMINATION BASED ON SHAPE OF COLONY |
| | WEIGHT — UNIFORMITY :LARGE / SHAPE OF COLONY :SMALL | WEIGHT — UNIFORMITY :LARGE / SHAPE OF COLONY :SMALL | WEIGHT — CIRCULARITY: SMALL / APPROXIMATION OF OUTWARD SHAPE OF CELL TO COMBINATION PATTERN OF A PLURALITY OF CIRCLES: LARGE / INTERNAL DEFECT: LARGE |

SINGLE STEM CELL SEEDING → EXCHANGE OF CULTURE MEDIUM AND ADDITION OF DRUGS

THERE ARE NO DIFFERENT TYPES OF CELLS

STEM CELL

COLONY   STEM CELL

STEM CELL

COLONY

COLONY

STEM CELL

STEM CELL

COLONY

FIG. 12

| TIME ELAPSED (MATURITY) | INITIAL STAGE OF SEEDING | STAGE AFTER LAPSE OF A FEW DAYS FROM SEEDING | STAGE AFTER LAPSE OF A WEEK FROM SEEDING |
|---|---|---|---|
| OPTICAL SYSTEM OF IMAGING DEVICE | PHASE CONTRAST MICROSCOPE | PHASE CONTRAST MICROSCOPE | DIFFERENTIAL INTERFERENCE MICROSCOPE |
| OPTICAL MAGNIFICATION | HIGH | HIGH | LOW |
| RESOLUTION | HIGH | HIGH | LOW |
| EXPOSURE TIME | LONG | LONG | SHORT |
| AMOUNT OF EXPOSURE | LARGE | LARGE | SMALL |
| WAVELENGTH OF ILLUMINATION LIGHT | SHORT | SHORT | LONG |

CELL IMAGE EVALUATION DEVICE, METHOD, AND PROGRAM

CROSS REFERENCE TO RELATED APPLICATIONS

The present application is a Continuation of PCT International Application No. PCT/JP2014/004206 filed on Aug. 18, 2014, which claims priority under 35 U.S.C. § 119(a) to Japanese Patent Application No. 2013-172380 filed on Aug. 22, 2013 and Japanese Patent Application No. 2014-043255 filed on Mar. 5, 2014. Each of the above applications is hereby expressly incorporated by reference, in its entirety, into the present application.

BACKGROUND OF THE INVENTION

1. Field of the Invention

The present invention relates to a cell image evaluation device and method and a program which evaluate a captured cell image.

2. Description of the Related Art

A pluripotent stem cell, such as an ES cell or an iPS cell, has the capability to be differentiated to cells of various tissues and has drawn attention since it can be applied to, for example, regenerative medicine, the development of drugs, and the interpretation of disease.

The stem cell is seeded in a scaffolding material (culture bed) in a culture container which is provided in a cell culture device and is multiplied in the scaffolding material using a culture medium (culture fluid) as nourishment. The multiplied stem cells are grown as a stem cell colony while being repeatedly agglutinated and combined with each other.

In the growth process of the stem cell, once the stem cell starts to be differentiated to a certain tissue, it is difficult to change and grow the stem cell to a different tissue while the stem cell is being differentiated. Therefore, it is important to multiply the stem cell to a sufficient number of stem cells while maintaining the stem cells in an undifferentiated state, and to differentiate the stem cells to a target tissue in the subsequent process, in terms of productivity.

There is a technique which cuts out only the region which is less likely to be undifferentiated in a stem cell colony and transplants the cut region to another culture container to perform subculturing. However, when the subculturing is performed, it is necessary to extract only the undifferentiated stem cell. That is, when the stem cell is cultured, it is necessary to appropriately evaluate the differentiation and undifferentiation of the stem cell.

For example, JP2012-95627A and JP2011-229410A disclose a technique which captures an image of a stem cell over time, checks a change in the observation image over time, and evaluates the undifferentiation and differentiation of the stem cell.

JP4852890B discloses a technique which evaluates the undifferentiation and differentiation of a stem cell, using tens of types of feature amounts including, for example, the number of stem cells and the number of nucleoli.

In addition to the above-mentioned stem cell undifferentiation and differentiation evaluation techniques, for example, a method has been proposed which captures an image of a cell obtained by inducing a stem cell to be differentiated to a target tissue, such as a cardiac muscle or a skin, or a cancer cell, with a microscope, checks the characteristics of the image, and evaluates the cultured state of the cell.

SUMMARY OF THE INVENTION

However, when the undifferentiation and differentiation of the stem cell are evaluated as described in JP2012-95627A, JP2011-229410A, and JP4852890B, the characteristics of the stem cell, such as the distribution state of the stem cell and the shape of the stem cell colony, are changed with the growth of the stem cell from the start of seeding. Therefore, in some cases, even when the undifferentiation and differentiation are evaluated on the basis of the same criteria, different evaluation results are obtained.

For example, in general, when the outward shape of the stem cell colony is close to a circle, the stem cell colony can be estimated to be maintained in an undifferentiated state. However, with the growth of the stem cell colony, the stem cell colony starts to be combined with a neighboring stem cell colony. As a result, the stem cell colony is maintained in the undifferentiated state, but does not have a circular shape. Therefore, the evaluation based on the degree of circularity of the outward shape of the stem cell is meaningless.

In general, when the density of cells is high, the cell can be evaluated to be maintained in the undifferentiated state. However, immediately after the stem cell is seeded, the maturity of the stem cell is not enough to form a stem cell colony. Therefore, the stem cell is maintained in the undifferentiated state, but the density of the stem cells is low. For this reason, the evaluation based on the density of the stem cells is insignificant.

In addition, a stem cell growth method or the characteristics of the stem cell vary depending on the culture conditions including, for example, a culture medium or scaffold used to culture the stem cell and a seeding method. Therefore, in some cases, even when the undifferentiation and differentiation are evaluated on the basis of the same criteria, different evaluation results are obtained.

The invention has been made in view of the above-mentioned problems and an object of the invention is to provide a cell image evaluation device and method and a program which can appropriately evaluate the state of a cell colony in each growth stage until a stem cell is grown to a certain level after the seeding of the stem cell.

According to an aspect of the invention, there is provided a cell image evaluation device including: an image acquisition unit that acquires a captured image of a cell; a cell evaluation unit that evaluates the cell image; and a maturity information acquisition unit that acquires information related to maturity of the cell. The cell evaluation unit determines a method for evaluating the cell image on the basis of the information related to the maturity.

In the cell image evaluation device according to the above-mentioned aspect of the invention, the cell evaluation unit may evaluate the cell image using plural types of evaluation criteria.

The cell evaluation unit may give different weights to the plurality of evaluation criteria and evaluate the cell image.

The plural types of evaluation criteria may include an evaluation criterion based on uniformity of a distribution of the cells and an evaluation criterion based on a shape of a colony of the cells.

The cell evaluation unit may set the weights such that a weight on an outward shape of the cell colony when the maturity is equal to or greater than a predetermined value is greater than a weight on the outward shape of the cell colony when the maturity is less than the predetermined value and evaluate the cell image.

When the maturity is equal to or greater than the predetermined value, the cell evaluation unit may evaluate the cell image, using the uniformity of brightness of the cell image as the evaluation criteria.

When the maturity is equal to or greater than the predetermined value, the cell evaluation unit may evaluate the cell image, using the uniformity of a thickness of the cell distributed in the cell image as the evaluation criteria.

When the maturity is equal to or greater than the predetermined value, the cell evaluation unit may evaluate the cell image, using the approximation between a combination pattern of a plurality of circles and the cell colony as the evaluation criteria.

The cell evaluation unit may change the cell image evaluation method on the basis of culture conditions of the cell.

When the culture conditions are that a cell different from the cell is used, the cell evaluation unit may perform a process of separating an image of the different cell from the cell image.

In a case in which the maturity is in an initial stage of seeding, the cell evaluation unit may perform a process of extracting the colony from the cell image when the culture condition is the seeding of the cell colony and may not perform the process of extracting the colony from the cell image when the culture condition is the seeding of a single cell.

According to another aspect of the invention, there is provided a cell image evaluation method including: when a captured image of a cell is acquired and the acquired cell image is evaluated, acquiring information related to maturity of the cell; and determining a method for evaluating the cell image on the basis of the acquired information related to the maturity.

According to still another aspect of the invention, there is provided a cell image evaluation program that causes a computer to function as: an image acquisition unit that acquires a captured image of a cell; a cell evaluation unit that evaluates the cell image; and a maturity information acquisition unit that acquires information related to maturity of the cell. The cell evaluation unit determines a method for evaluating the cell image on the basis of the information related to the maturity.

According to the cell image evaluation device and method and the program of the invention, when a captured cell image is acquired and the cell image is evaluated, information related to the maturity of the cell is acquired and a method for evaluating the cell image is determined on the basis of the acquired information related to the maturity. Therefore, it is possible to appropriately evaluate the state of a cell colony in each growth stage from the start of the seeding of cells to a certain growth stage.

BRIEF DESCRIPTION OF THE DRAWINGS

FIG. 2 is a table illustrating an example of an undifferentiation and differentiation evaluation method corresponding to the maturity and culture conditions of a stem cell.

FIG. 3 is a table illustrating an example of the undifferentiation and differentiation evaluation method corresponding to the maturity and culture conditions of a stem cell.

FIG. 4 is a table illustrating an example of the undifferentiation and differentiation evaluation method corresponding to the maturity and culture conditions of the stem cell.

FIG. 12 is a table illustrating an example of an imaging method corresponding to the maturity of a stem cell.

DESCRIPTION OF THE PREFERRED EMBODIMENTS

Figure 1:
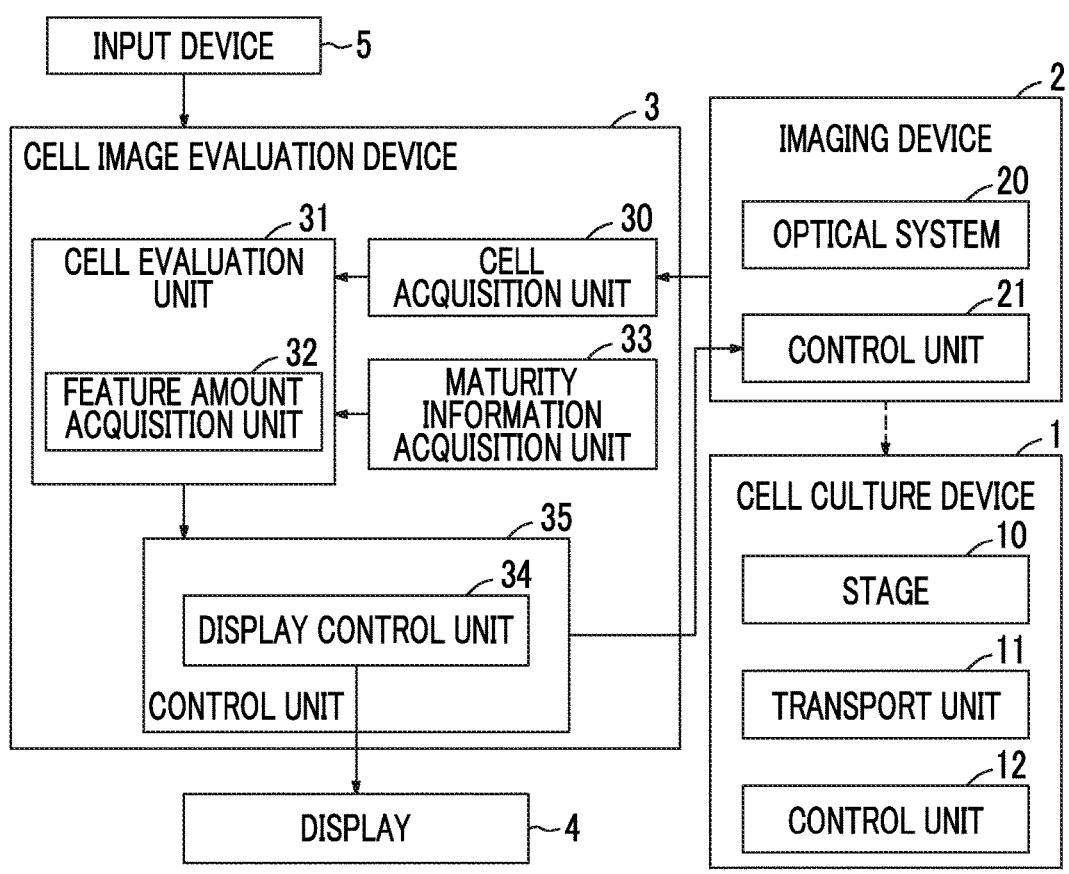
FIG. 1 is a block diagram schematically illustrating the structure of a cell culture observation system using a first embodiment of a cell image evaluation device according to the invention.

Hereinafter, an embodiment of a cell image evaluation device and method and a program according to the invention will be described in detail with reference to the drawings. The invention is characterized in a method for evaluating a captured cell image. First, the overall structure of a cell culture observation system including an embodiment of the cell image evaluation device according to the invention will be described. FIG. 1 is a block diagram schematically illustrating the structure of the cell culture observation system.

As illustrated in FIG. 1, the cell culture observation system according to this embodiment includes a cell culture device 1, an imaging device 2, a cell image evaluation device 3, a display 4, and an input device 5.

The cell culture device 1 is used to culture cells. Examples of the cell to be cultured include pluripotent stem cells, such as iPS cells or ES cells, nerve cells, skin cells, cardiac muscle cells, and liver cells which are differentiation-induced from stem cells, and cancer cells. The cell culture device 1 includes a plurality of culture containers in which the cells to be cultured are seeded in a culture medium. The cell culture device 1 includes a stage 10, a transport unit 11, and a control unit 12.

The culture container whose image is to be captured by the imaging device 2 is placed on the stage 10. The transport unit 11 selects the culture container whose image is to be captured from a plurality of culture containers which are accommodated at predetermined positions in the cell culture device 1 and transports the selected culture container to the stage 10. The control unit 12 controls the overall operation of the cell culture device 1 and controls environmental conditions, such as temperature, humidity, and $CO_2$ concentration, in the cell culture device 1, in addition to the operation of the stage 10 or the transport unit 11. A known structure can be used to adjust the temperature, humidity, and $CO_2$ concentration.

The imaging device 2 captures the image of the cell in the culture container placed on the stage 10. The imaging device 2 includes an optical system 20 which captures the image of the cell and outputs the cell image and a control unit 21 which controls the optical system 20.

The optical system 20 includes a phase contrast microscope and a differential interference microscope. The capture of a cell image by the phase contrast microscope and the capture of a cell image by the differential interference microscope are switched according to the culture maturity of the stem cell in the culture container.

These microscopes include an imaging element such as a complementary metal-oxide semiconductor (CMOS) sensor or a charge-coupled device (CCD) sensor. The captured cell image is output from the imaging element. The switching between the imaging operations of the microscopes will be described in detail below.

The control unit 21 controls the overall operation of the imaging device 2. Particularly, in this embodiment, the control unit 21 controls, for example, the switching between the capture of the cell image by the phase contrast microscope and the capture of the cell image by the differential interference microscope, the optical magnification of the optical system 20, the exposure time or resolution of the imaging element, the amount of light emitted from an illumination light source which is provided in the optical system 20, or the switching between the wavelengths of illumination light. The control unit 21 changes an imaging method, depending on the maturity of a stem cell, on the basis of a control signal output from the control unit 35 of the cell image evaluation device 3, which will be described in detail below. For the switching between the capture of the cell image by the phase contrast microscope and the capture of the cell image by the differential interference microscope, for example, the position where the culture container is provided may be switched to the imaging position of the phase contrast microscope and the imaging position of the differential interference microscope.

An embodiment of a cell image evaluation program according to the invention is installed in a computer to implement the cell image evaluation device 3.

The cell image evaluation device 3 includes, for example, a central processing unit, a semiconductor memory, and a hard disk and an embodiment of the cell image evaluation program according to the invention is installed in the hard disk. When the control unit 35 including a central processing unit executes the program, a cell image acquisition unit 30 (corresponding to an image acquisition unit), a cell evaluation unit 31, a maturity information acquisition unit 33, and a display control unit 34 illustrated in FIG. 1 operate.

The cell image acquisition unit 30 acquires the cell image captured by the imaging device 2 and stores the acquired cell image. In addition, the cell image acquisition unit 30 outputs the acquired cell image to the cell evaluation unit 31 and the display control unit 34.

The cell evaluation unit 31 evaluates, for example, the state of the cell on the basis of the cell image acquired by the cell image acquisition unit 30. In this embodiment, the cell evaluation unit 31 evaluates the undifferentiation and differentiation of the stem cell.

The cell evaluation unit 31 includes a feature amount acquisition unit 32 which acquires various feature amounts from the cell image and evaluates the undifferentiation and differentiation of the stem cell, on the basis of the feature amounts acquired by the feature amount acquisition unit 32. In addition, the cell evaluation unit 31 changes a method for evaluating the undifferentiation and differentiation of the stem cell, depending on the maturity of the stem cell or the culture conditions of the stem cell. Here, a change in the evaluation method means, for example, a change in evaluation criteria used to evaluate undifferentiation and differentiation or a change in a weight on each evaluation criterion when undifferentiation and differentiation are evaluated using a plurality of evaluation criteria.

In this embodiment, the cell evaluation unit 31 changes the undifferentiation and differentiation evaluation method, depending on maturity which is divided into three stages, that is, an initial stage in the seeding of the stem cell, a stage after a few days have elapsed since the seeding of the stem cell, and a stage after a week has elapsed since the seeding of the stem cell.

Information related to the maturity of the cell may be any information as long as it indicates the stage of the maturity of the cell. For example, a culture period which is measured by a timer can be acquired as the information related to the maturity. In addition, the information related to the maturity is not limited to the culture period. For example, the following information may be acquired as the information related to the maturity: the image information of a cell colony region in the cell image is analyzed to measure the size of the cell colony, the number of cells in the cell colony, or the number of cells in a unit area smaller than the cell colony and maturity increases as the measured number of cells increases. For example, the area, peripheral length, and maximum diameter of the cell colony can be acquired as the size of the cell colony.

For example, the brightness of the image of the cell colony region or texture, such as uniformity or roughness, may be acquired as the information related to the maturity. For example, when the cell whose image is to be captured is a stem cell, the density of the stem cells increases as the maturity of the stem cell increases. In addition, the stem cells are stacked and the brightness of the image increases gradually. Therefore, as the brightness increases, the maturity increases.

When the maturity increases and the stem cells are multiplied and stacked, the uniformity of the image increases and a smooth image with little unevenness is obtained. Therefore, the maturity increases as the uniformity of the image increases or the image becomes smoother. A known method can be used as a method for acquiring feature amounts such as the uniformity and smoothness of the image.

The feature amounts of the shape of a stem cell colony may be acquired as the information related to the maturity. When the maturity of the stem cell increases, the shape of the stem cell colony becomes gradually similar to a circle and the differentiation of a peripheral portion of the stem cell progresses, which results in an increase in the complexity of the edge. Therefore, the feature amounts of a change in the shape of the stem cell colony can be acquired as the information related to the maturity.

In addition, the feature amounts of the thickness of the stem cell colony may be acquired as the information related to the maturity. As the maturity of the stem cell increases, the thickness of the stem cell colony increases gradually. Therefore, the feature amounts of the thickness of the stem cell colony can be acquired as the information related to the maturity. The thickness of the stem cell colony may be measured by a measurement device which is separately provided or the user may set and input the thickness of the stem cell colony, using the input device 5.

In addition, the user may set and input the passage number of the cell as the information related to the maturity, using the input device 5.

The maturity information acquisition unit 33 acquires the information related to the maturity of the cell and acquires the stage of the maturity of the cell from the information.

In this embodiment, the maturity is divided into three stages as described above. However, the maturity is not limited to three stages and may be divided into two stages or four or more stages. In addition, various gaps may be set between the levels according to, for example, culture conditions.

In this embodiment, the cell evaluation unit 31 acquires, as the culture conditions, the condition of whether different types of cells are cultured and the condition of whether a seeding method is a colony seeding method which seeds each colony or a single cell seeding method which seeds each stem cell.

When a stem cell is cultured, in some cases, a cell that is a different type from the stem cell to be cultured is used. The stem cell is grown in different ways when different types of stem cells are cultured and when the stem cell is cultured without a different type of cell. In addition, while the stem cell is being cultured, in some cases, the culture media are exchanged and drugs are added. In this case, the type of culture medium to be exchanged or the type of drug varies, depending on whether different types of cells are cultured or the stem cell is cultured without a different type of cell and the state of the stem cell which is being cultured. In addition, a method for growing the stem cell varies depending on the culture conditions. Therefore, it is preferable to change criteria for evaluating undifferentiation and differentiation.

For this reason, in this embodiment, the cell evaluation unit 31 acquires the condition of whether different types of cells are cultured and the condition of whether the exchange of the culture medium and the addition of drugs are performed and changes the undifferentiation and differentiation evaluation method, depending on these conditions. In addition, the cell evaluation unit 31 may acquire conditions, such as the type of culture medium to be exchanged during culture and the type of drug to be added, and may change the undifferentiation and differentiation evaluation method, depending on these conditions.

When a stem cell is cultured, there are the following stem cell seeding method: a colony seeding method which seeds each colony; and a single cell seeding method which seeds each stem cell. In the colony seeding method and the single cell seeding method, different image processing methods are used to extract feature amounts used to evaluate undifferentiation and differentiation and the stem cell is grown in different ways. Therefore, it is preferable to change the criteria for evaluating undifferentiation and differentiation. For this reason, in this embodiment, the cell evaluation unit 31 acquires the conditions of the seeding method and changes the undifferentiation and differentiation evaluation method, depending on the acquired conditions of the seeding method.

The user may set and input the above-mentioned culture conditions using the input device 5 and the cell evaluation unit 31 may acquire the input culture conditions. In addition, the culture conditions are not limited to the above-mentioned culture conditions. For example, other culture conditions which affect the progress of the growth of the stem cell, such as information about the type of culture medium or scaffold, may be used.

The feature amount acquisition unit 32 acquires feature amounts which correspond to the evaluation criteria in each evaluation method corresponding to the maturity of the stem cell or the culture conditions.

Next, each evaluation method corresponding to each stage of the maturity of the stem cell and the culture conditions will be described in detail with reference to the tables illustrated in FIGS. 2 to 4.

First, the evaluation methods corresponding to each stage of the maturity when the culture conditions are that different types of cells are cultured and the seeding method is the colony seeding method will be described with reference to FIG. 2.

First, when the maturity of the stem cell is an initial seeding level, the phase contrast microscope of the imaging device 2 is used to capture a cell image and the feature amount acquisition unit 32 performs image processing for separating a stem cell colony from a different type of cells and extracting the stem cell colony in the cell image. Since the difference between the size of the different type of cells and the stem cell colony is an order unit, edge detection or pattern matching can be performed to separate the stem cell colony from a different type of cells and to extract only the stem cell colony.

In this stage, the cell evaluation unit 31 evaluates undifferentiation and differentiation, using the shape of the extracted stem cell colony and the uniformity of each stem cell in the stem cell colony as the evaluation criteria.

Specifically, the feature amount acquisition unit 32 extracts an outer circumferential shape and an internal defect as information about the shape of the stem cell colony. In general, when the stem cell is not differentiated, the shape of the stem cell colony is close to a circle. When the differentiation of the stem cell progresses, the stem cell is separated and the circular shape of the stem cell colony is broken. Therefore, the degree of circularity of the outer circumferential shape of the stem cell colony can be evaluated to evaluate the undifferentiation and differentiation of the stem cell colony. In addition, the internal defect of the stem cell colony is, for example, a hole which is formed in the stem cell colony by differentiation.

The feature amount acquisition unit 32 acquires the distribution state of each stem cell in the stem cell colony and acquires information indicating the uniformity of the distribution of each stem cell. When the stem cells are uniformly distributed, the stem cells are likely to be undifferentiated. When the stem cells are distributed so as to be concentrated on a portion and the distribution of the stem cells is not uniform, the stem cells are likely to be differentiated.

The distribution state of each stem cell in the stem cell colony may be acquired by detecting the pattern of nucleoli in the stem cell or by detecting the pattern of halos which occur due to diffracted light passing between the stem cells. When illumination light passes between the stem cells, diffraction occurs. When the distance (slit gap) between the stem cells is an integer multiple of the wavelength of the illumination light, the phases of diffracted light (positive and negative first-order diffracted light) and direct light (zerothorder diffracted light) are synthesized and an artifact with high brightness is generated. The artifact with high brightness is halo.

Then, the cell evaluation unit 31 calculates an evaluation value related to the degree of circularity of the outer circumferential shape of the stem cell colony, an evaluation value related to whether there is an internal defect or the size of the internal defect, an evaluation value related to the uniformity of each stem cell in the stem cell colony. Then, the cell evaluation unit 31 weights the evaluation values and adds the weighted evaluation values to calculate a final evaluation value for evaluating undifferentiation and differentiation. When the evaluation value is equal to or greater than a predetermined threshold value, the cell evaluation unit 31 evaluates that the stem cell has not been differentiated. When the evaluation value is less than the threshold value, the cell evaluation unit 31 evaluates that the stem cell has been differentiated.

In this case, a weight on the evaluation value related to the uniformity of the stem cell is greater than a weight on the evaluation value related to the shape of the stem cell colony (the outer circumferential shape and the internal defect).

Figure 5:
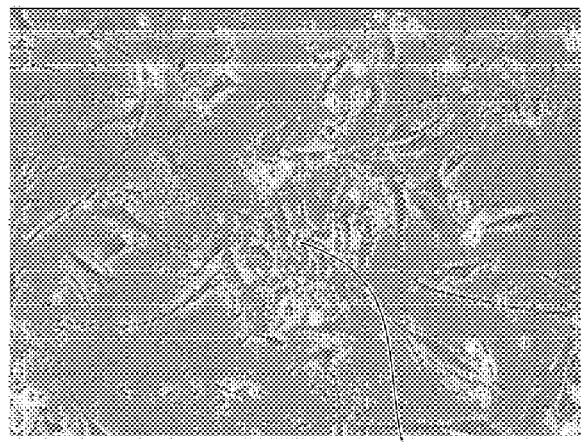
FIG. 5 is a diagram illustrating an example of an observation image of a stem cell in an initial stage of seeding.

The reason is as follows. When the maturity of the stem cell is in the initial stage of seeding, as illustrated in FIG. 5, the maturity of the stem cell colony is low. Therefore, in some cases, the outer circumferential shape of the stem cell colony is not a circle or a gap which is not related to differentiation is formed between the stem cells in the stem cell colony. The weight on the evaluation of the uniformity of the distribution of the stem cells is greater than the weight on the evaluation of the shape of the stem cell colony, in order to accurately evaluate undifferentiation and differentiation.

When the maturity of the stem cell is in the stage after a few days have elapsed since seeding, similarly to the initial stage of seeding, the phase contrast microscope is used to capture a cell image and the feature amount acquisition unit 32 performs image processing for extracting a stem cell colony from the cell image.

Then, in this stage, the cell evaluation unit 31 evaluates undifferentiation and differentiation, using the shape of the extracted stem cell colony and the uniformity of individual stem cells in the stem cell colony as evaluation criteria. However, the weight is different from that in the initial stage of seeding.

Specifically, in this stage, the cell evaluation unit 31 sets weights on the evaluation values such that a weight on the evaluation value of the uniformity of the stem cell is greater than a weight on the evaluation value of the shape of the stem cell colony. In this case, the weight on the evaluation value for the shape of the stem cell colony is greater than the weight on the evaluation value of the shape of the stem cell colony in the initial stage of seeding.

Figure 6:
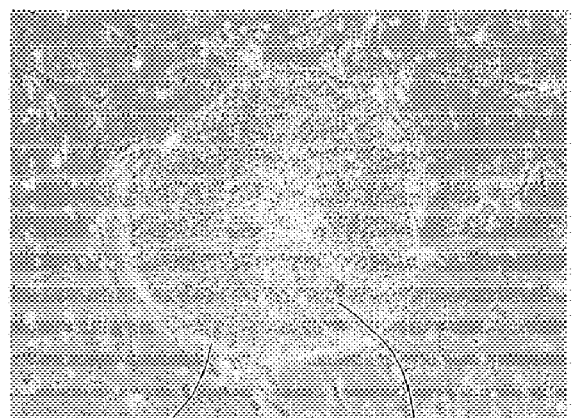
FIG. 6 is a diagram illustrating an example of the observation image of the stem cell in a stage after a few days have elapsed since the seeding.

The reason is considered as follows. In the stage after a few days have elapsed since the seeding, as illustrated in FIG. 6, the maturity of the stem cell colony increases slightly, the outer circumferential shape of the stem cell colony is close to a circle, and the density of the stem cells in the stem cell colony increases. Therefore, the weight on the evaluation value of the shape of the stem cell colony increases in order to accurately evaluate undifferentiation and differentiation.

When the maturity of the stem cell is in the stage after a week has elapsed since the seeding, the imaging device 2 captures a cell image, using not the phase contrast microscope, but the differential interference microscope, and the feature amount acquisition unit 32 performs image processing for separating a different type of cells from the stem cell colony in the cell image and extracting the stem cell colony.

Figure 7:
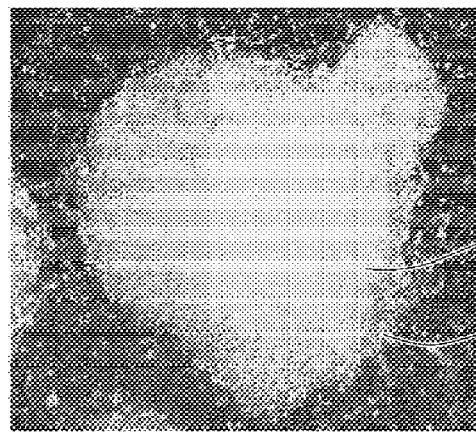
FIG. 7 is a diagram illustrating an example of the observation image of the stem cell in a stage after a week has elapsed since the seeding.

In this stage, in some cases, the growth of the stem cell colony is developed and the stem cells are stacked as illustrated in FIG. 7. As such, when the stem cells are stacked, a diffracted light component and a refracted light component from the stacked stem cells overlap each other. As a result, it is difficult to separate diffracted light from one stem cell and the light intensity of the entire image increases. Therefore, it is difficult to measure the micro-characteristics of each stem cell in the stem cell colony with the phase contrast microscope. For this reason, in this stage, as described above, the cell image is captured by the differential interference microscope.

In this stage, the cell evaluation unit 31 evaluates undifferentiation and differentiation, using the shape of the stem cell colony, the uniformity of the brightness of the stem cell colony, and the uniformity of the thickness of the stem cell colony as the evaluation criteria.

Specifically, the feature amount acquisition unit 32 extracts the outer circumferential shape and internal defect of the stem cell colony, similar to the previous stage. In addition, the feature amount acquisition unit 32 acquires the distribution of the brightness signal in the stem cell colony and acquires the uniformity of the brightness signal. Furthermore, the feature amount acquisition unit 32 acquires the uniformity of the thickness of the stem cell colony. The thickness of the stem cell colony can be measured by an interferometer such as optical coherence tomography (OCT).

For example, the standard deviation of the brightness signal or the thickness may be acquired as the uniformity of the brightness signal or the thickness, or the difference between the maximum value and the minimum value may be acquired as the uniformity of the brightness signal or the thickness. When the brightness signal or the thickness is uniformly distributed, the stem cell is likely to be undifferentiated. When portions with a higher or lower brightness than the surroundings or portions with a larger or smaller thickness than the surroundings are non-uniformly distributed so as to be concentrated, the stem cell is likely to be differentiated.

The cell evaluation unit 31 calculates an evaluation value related to the degree of circularity of the outer circumferential shape of the stem cell colony, an evaluation value related to the approximation of the outer circumferential shape to a combination pattern of a plurality of circles, an evaluation value related to whether there is an internal defect or the size of the internal defect, an evaluation value related to the uniformity of brightness, and an evaluation value related to the uniformity of the thickness, weights the evaluation values, and adds the weighted evaluation values to calculate a final evaluation value for evaluating undifferentiation and differentiation. The approximation of the outer circumferential shape to a combination pattern of a plurality of circles means the degree of approximation between the outer circumferential shape of the stem cell colony and a combination pattern of a plurality of circles.

In this case, for the weights on each evaluation value, the weight on the evaluation value related to the degree of circularity is relatively small and the weights on the evaluation values related to the approximation of the outer circumferential shape to a combination pattern of a plurality of circles, the internal defect, the uniformity of the brightness, and the uniformity of the thickness are relatively large.

Figure 8:
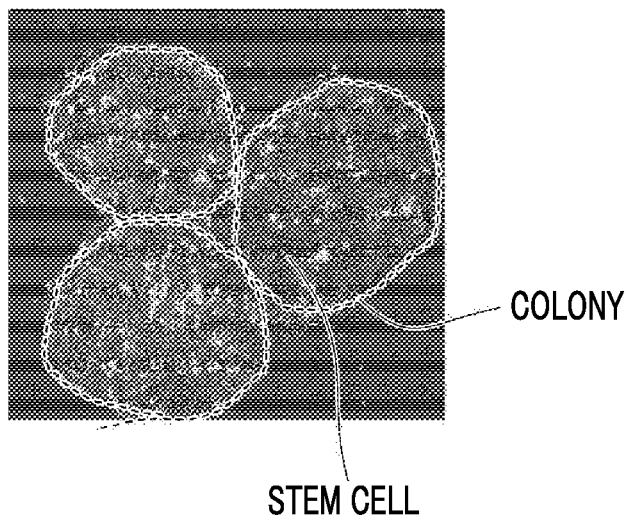
FIG. 8 is a diagram illustrating an example of the observation image of the stem cell in the stage after a week has elapsed since the seeding.

When the maturity of the stem cell is in the stage after a week has elapsed since the seeding, in some cases, the stem cell colonies are combined with each other and the outer circumferential shape of the stem cell colony is not maintained in a circle, as illustrated in FIG. 8. For this reason, the weight on the evaluation value related to the degree of circularity is set to a small value and the weight corresponding to, for example, the evaluation value related to the approximation of the outer circumferential shape to a combination pattern of a plurality of circles is set to a large value, which makes it possible to accurately evaluate undifferentiation and differentiation.

The evaluation method corresponding to each maturity stage when the culture conditions are that different types of cells are cultured and the cell colony seeding method is used has been described above.

Next, an evaluation method corresponding to each maturity stage when the culture conditions are that different types of cells are cultured and the single cell seeding method is used will be described with reference to FIG. 2.

In this case, in the single cell seeding method, only the evaluation method when the maturity of the stem cell is in the initial stage of seeding differs from that in the colony seeding method, and the evaluation method when the maturity of the stem cell is the stage after a few days have elapsed since the seeding and the evaluation method when the maturity of the stem cell is the stage after a week from seeding are the same as those in the colony seeding method.

When different types of cells are cultured and the single cell seeding method is used, a cell image is captured by the phase contrast microscope, similarly to the colony seeding method. However, in this case, since no colony has been formed in the initial stage of seeding, image processing for extracting the colony is not performed, unlike the colony seeding method.

Then, similarly to the colony seeding method, the feature amount acquisition unit 32 extracts the outer circumferential shape and internal defect of the stem cell colony. However, in this stage, the colony is not clearly formed, as described above. Therefore, the feature amount acquisition unit 32 specifies the region in which the stem cell colony is estimated to be formed from the distribution state of the stem cells and extracts the outer circumferential shape and internal defect of the specified region.

In addition, the feature amount acquisition unit 32 acquires the distribution state of a different type of cells and the stem cells and acquires the uniformity of the distribution of these cells. In this case, since it is difficult to distinguish the stem cell from a different type of cells, the uniformity of both cells is acquired.

Then, the cell evaluation unit 31 calculates an evaluation value related to the degree of circularity of the outer circumferential shape of the stem cell colony, an evaluation value related to whether there is an internal defect or the size of the internal defect, and an evaluation value related to the uniformity of the stem cell and the different type of cells, weights the evaluation values, and adds the weighted evaluation values to calculate a final evaluation value for evaluating undifferentiation and differentiation. In this case, the weight on the evaluation value related to the uniformity of the stem cell is greater than the weight on the evaluation value related to the thickness of the stem cell colony (the outer circumferential shape and the internal defect).

The upper part of FIG. 3 illustrates an evaluation method corresponding to each maturity stage when the culture conditions are that the stem cell is cultured without a different type of cells and the colony seeding method is used. In this case, the evaluation methods corresponding to all of the maturity stages are the same as those when different types of cells are cultured and the colony seeding method is used.

The lower part of FIG. 3 illustrates an evaluation method corresponding to each maturity stage when the stem cell is cultured without a different type of cells and the single cell seeding method is used. In this case, the evaluation method when the maturity of the stem cell is in the initial stage of seeding and the evaluation method when the maturity of the stem cell is in the stage after a few days have elapsed since seeding are the same as those when the different types of cells are cultured and the single cell seeding method is used, and only the evaluation method when the maturity of the stem cell is in the stage after a week has elapsed since the seeding is different from that when the different types of cells are cultured and the single cell seeding method is used.

Specifically, when the stem cell is cultured without a different type of cells and the single cell seeding method is used, in the stage after a week has elapsed since the seeding, a cell image is not captured by the differential interference microscope, but is captured by the phase contrast microscope. The feature amount acquisition unit 32 performs image processing for separating the stem cell colony from a different type of cells and extracting the stem cell colony in the cell image.

Figure 9:
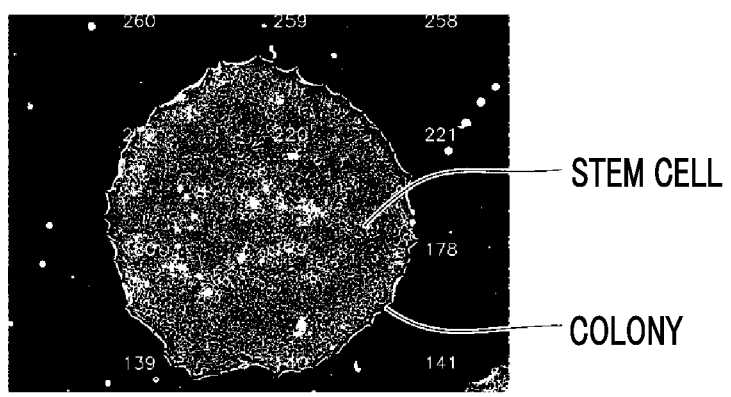
FIG. 9 is a diagram illustrating an example of the observation image when a stem cell colony is grown so as to extend in a plane direction.

The reason why the cell image is not captured by the differential interference microscope, but is captured by the phase contrast microscope is as follows. When different types of cells are cultured, in some cases, the stem cells are stacked by the growth of the stem cell colony. When the stem cell is cultured without a different type of cells and the single cell seeding method is used, it takes a lot of time until the stem cells are stacked. For a period of about a week, as illustrated in FIG. 9, the stem cell colony is grown so as to extend in the plane direction. When the step cell is cultured without a different type of cells and the colony seeding method is used, the stem cell colony is grown earlier than that when the single cell seeding method is used and the stem cells are likely to be stacked. For this reason, the cell image is captured by the differential interference microscope as described above.

Then, the cell evaluation unit 31 weights the evaluation value related to the degree of circularity of the outer circumferential shape of the stem cell colony, the evaluation value related to the approximation of the outer circumferential shape to a combination pattern of a plurality of circles, and the evaluation value related to whether there is an internal defect or the size of the internal defect and adds the weighted evaluation values to calculate a final evaluation value for evaluating undifferentiation and differentiation. However, the calculation of the evaluation value related to the uniformity of brightness and the uniformity of thickness is not considered. For the weight on each evaluation value, similarly to the case in which different types of cells are cultured, the evaluation value related to the degree of circularity is relatively small and the evaluation values related to the approximation of the outer circumferential shape to a combination pattern of a plurality of circles and the internal defect are relatively large.

FIG. 4 illustrates the evaluation method corresponding to each maturity stage when the culture conditions are that the step cell is cultured without a different type of cells, the single cell seeding method is used, and the exchange of the culture medium and the addition of drugs are performed before a few days have elapsed since the seeding of the stem cell.

In the case of the culture conditions, the evaluation method in the initial stage of seeding and the evaluation method in the stage after a week has elapsed seeding are the same as those when the stem cell is cultured without a different type of cells, the single cell seeding method is used, and the culture medium and the addition of drugs are not performed. When the exchange of the culture medium and the addition of drugs are performed after a few days have elapsed since the seeding, undifferentiation and differentiation are evaluated, on the basis of the same evaluation criteria as those in the initial stage of seeding, in order to evaluate the effect obtained by the addition of the drugs using the same evaluation criteria as those in the evaluation method before the drugs are added.

The undifferentiation and differentiation evaluation method of the cell evaluation unit 31 according to this embodiment has been described above.

Returning to FIG. 1, the display control unit 34 displays the cell image acquired by the cell image acquisition unit 30 on the display 4 or displays the evaluation result of undifferentiation and differentiation by the cell evaluation unit 31 on the display 4. The display control unit 34 may display the feature amounts or the evaluation values used for evaluation as well as the evaluation result on the display 4.

The control unit 35 controls the overall operation of the cell image evaluation device 3 and outputs a control signal to the control unit 21 of the imaging device 2 such that a cell image capture method is changed depending on information related to the maturity acquired by the maturity information acquisition unit 33.

The input device 5 includes, for example, a mouse or a keyboard and receives an operation input by the user. For example, the input device 5 receives the setting or change of the evaluation criteria for evaluating undifferentiation and differentiation or receives the setting or change of the weights used to calculate the evaluation values.

Figure 10:
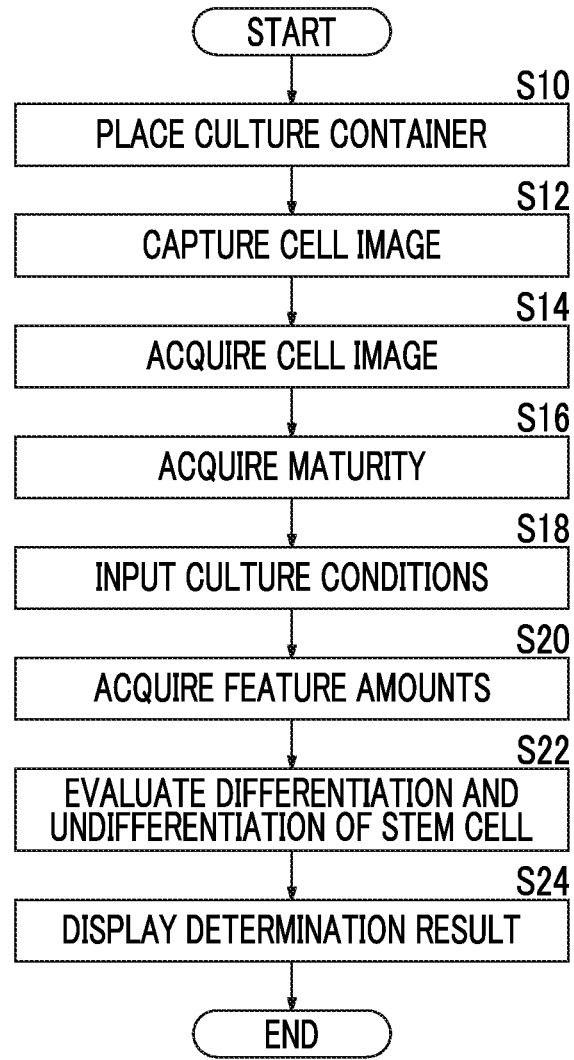
FIG. 10 is a flowchart illustrating the operation of the cell culture observation system illustrated in FIG. 1.

Next, the operation of the stem cell culture observation system will be described with reference to the flowchart illustrated in FIG. 10.

First, in the cell culture device 1, the transport unit 11 selects the culture container whose image is to be captured from a plurality of culture containers provided in cell culture device 1 and the selected culture container is placed on the stage 10 (S10).

Figure 11:
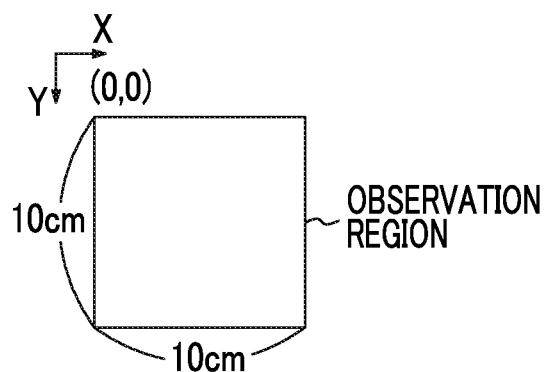
FIG. 11 is a diagram illustrating an example of an observation region.

Then, a cell image of an observation region including the stem cell in the culture container is captured by the phase contrast microscope or the differential interference microscope of the imaging device 2 (S12). Specifically, 40 shots× 40 shots of images of a rectangular observation region with a size of 10 cm×10 cm illustrated in FIG. 11 are captured by the phase contrast microscope to acquire one cell image.

Then, the cell image captured by the imaging device 2 is output to the cell image evaluation device 3 and is then acquired by the cell image acquisition unit 30 of the cell image evaluation device 3 (S14).

In this case, the maturity information acquisition unit 33 acquires, for example, the culture period at the time when the cell image is captured as the information related to the maturity (S16) and culture conditions are input by the user through the input device 5 (S18).

Then, the cell image acquired by the cell image acquisition unit 30, the information related to the maturity acquired by the maturity information acquisition unit 33, and the culture conditions input by the user are output to the cell evaluation unit 31 and the feature amount acquisition unit 32 acquires feature amounts corresponding to the maturity and the culture conditions, on the basis of the input cell image, maturity information, and culture conditions (S20).

Then, the cell evaluation unit 31 evaluates the undifferentiation and differentiation of the stem cell in the cell image on the basis of the feature amounts acquired by the feature amount acquisition unit 32, using an evaluation method corresponding to the maturity and culture conditions of the stem cell (S22).

The evaluation result of undifferentiation and differentiation by the cell evaluation unit 31 is output to the display control unit 34 and the display control unit 34 displays the input cell image and the input evaluation result of undifferentiation and differentiation on the display 4 (S24).

The cell culture observation system according to the above-described embodiment acquires the captured cell image of the stem cell, acquires information related to the maturity of the stem cell when the undifferentiation and differentiation of the cell image is evaluated, on the basis of the stem cell, and changes the method for evaluating undifferentiation and differentiation, on the basis of the information related to the maturity. Therefore, it is possible to appropriately evaluate the undifferentiation and differentiation of the stem cell in each growth stage until the stem cell is grown to a certain level after the seeding of the stem cell.

In addition, the method for evaluating undifferentiation and differentiation is changed depending on the culture conditions of the stem cell. Therefore, even when the culture conditions are different, it is possible to appropriately evaluate the undifferentiation and differentiation of the stem cell.

The evaluation criteria used to evaluate undifferentiation and differentiation are not limited to, for example, the uniformity of the stem cell, or the shape of the stem cell colony. For example, the density of the stem cells, the generation state of halos in the stem cell colony, or the definiteness of the boundary between the stem cell colonies may be used as the evaluation criteria.

In the above-described embodiment, in the initial stage of seeding and after a few days have elapsed since the seeding, the cell image is captured by the phase contrast microscope. In the stage after a week has elapsed since the seeding, the cell image is captured by the differential interference microscope. That is, the imaging method of the imaging device 2 is changed depending on the maturity of the stem cell. In addition, even in the stage after a week has elapsed since the seeding, the cell image is captured by the differential interference microscope when different types of cells are cultured and the cell image is captured by the phase contrast microscope when the stem cell is cultured without a different type of cells and the single cell seeding method is used. That is, the imaging method of the imaging device 2 is changed depending on the culture conditions.

As such, in addition to the structure in which the type of the optical system 20 is changed depending on the maturity or the culture conditions to change the imaging method, the imaging conditions of the optical system 20 or the imaging conditions of the imaging element may be changed to change the imaging method. In addition, a change from the phase contrast microscope to the differential interference microscope also means a change in an illumination method.

Next, a case in which imaging conditions are changed depending on the maturity or culture conditions of the stem cell will be described with reference to the table illustrated in FIG. 12.

First, in the initial stage of the seeding and the stage after a few days have elapsed since the seeding, it is preferable that the optical magnification of the optical system 20 is higher than that in the stage after a week has elapsed since the seeding, in order to give a greater weight to the evaluation of the distribution state of each stem cell than to the outward shape of the stem cell colony. In this case, it is possible to capture the image of each stem cell with high accuracy. In contrast, in the stage after a week has elapsed since the seeding, the optical magnification is relatively low. In this case, it is possible to capture the image of the overall shape of the stem cell colony. Therefore, it is possible to evaluate, for example, the approximation of the outer circumferential shape of the stem cell colony to a combination pattern of a plurality of circles or the internal defect of the stem cell colony with high accuracy.

For the same reason as described above, it is preferable that the resolution of the imaging element in the optical system 20 is relatively high in the initial stage of seeding and the stage after a few days have elapsed since the seeding and is relative low in the stage after a week has elapsed since the seeding. For a change in the resolution, for example, a plurality of imaging elements with different resolutions may be switched or binning may be performed for down-sampling when an image signal is read from one imaging element.

In the initial stage of seeding and the stage after a few days have elapsed since the seeding, the weight on the evaluation of the distribution state of each stem cell is greater than the weight on the evaluation of the outward shape of the stem cell colony. Therefore, it is preferable that the exposure time of the imaging element of the optical system 20 is set to be longer than that in the stage after a week has elapsed since the seeding, in order to detect, for example, the edge or halo of each stem cell with high accuracy. In this case, it is possible to capture the image of each stem cell with high accuracy.

Figure 13:
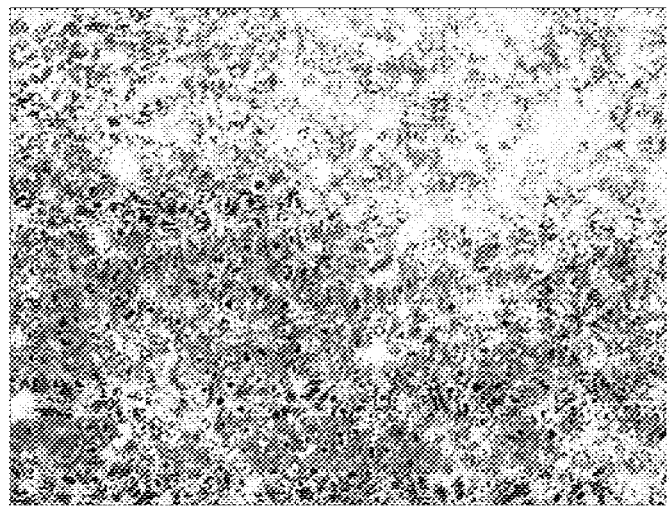
FIG. 13 is a diagram illustrating the stacked state of stem cell colonies.
Figure 14:
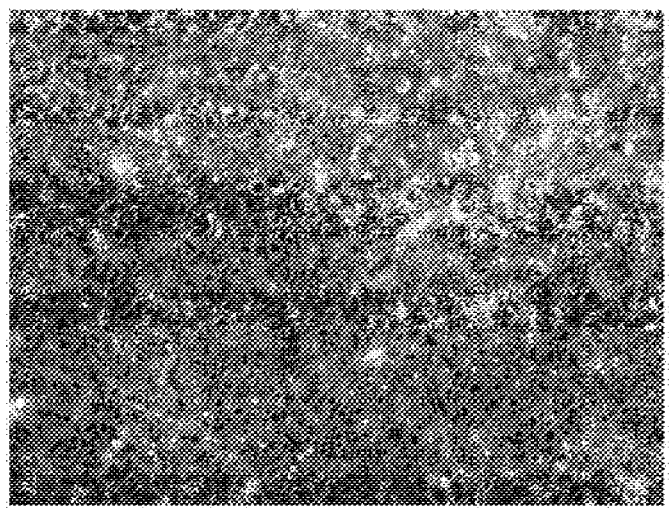
FIG. 14 is a diagram illustrating an observation image which is captured when the exposure time of the stem cell colony, of which the cell image illustrated in FIG. 13 is to be captured, is short.

In the stage after a week has elapsed since the seeding, the stem cell colonies are stacked as described above. A diffracted light component and a refracted light component from the stacked stem cells overlap each other, which results in an increase in the light intensity of the entire image. As a result, as illustrated in FIG. 13, white voids are generated in the cell image, which makes it difficult to accurately observe the state of the stem cell colony. Therefore, in the stage after a week has elapsed since the seeding, it is preferable that the exposure time of the imaging element is set to a relatively small value. FIG. 14 illustrates a cell image when the exposure time of the stem cell colony, of which the cell image illustrated in FIG. 13 is to be captured, is short.

For a change in the exposure time, the number of exposures may be changed to change the exposure time. For example, in the initial stage of seeding and the stage after a few days have elapsed since the seeding, the number of exposures may be two or more and a plurality of cell images may be added. In the stage after a week has elapsed since the seeding, the number of exposures may be one and a cell image may be acquired. A change in the number of exposures substantially corresponds to a change in the exposure time.

For the same reason as described above, in the initial stage of seeding and the stage after a few days have elapsed since the seeding, it is preferable that the amount of light from the light source of the optical system 20 is relatively large. In the stage after a week has elapsed since the seeding, it is preferable that the amount of light is relatively small.

In the initial stage of seeding and the stage after a few days have elapsed since the seeding, it is necessary to capture the image of the edge of each stem cell with high resolution and the wavelength of illumination light from the optical system 20 is preferably shorter than the wavelength of illumination light in the stage after a week has elapsed since the seeding. In this case, it is possible to increase a spatial resolution. In contrast, in the stage after a week has elapsed since the seeding, the image of the overall shape of the stem cell colony is captured and a very high spatial resolution is not required. When the wavelength of illumination light is short, strong light scattering occurs. Therefore, scattering occurs at the boundary between the stem cell and a portion which is not the stem cell and the boundary of the overall shape of the stem cell colony is blurred.

Figure 15:
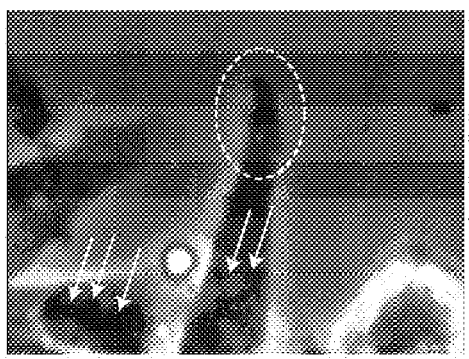
FIG. 15 is a diagram illustrating a phase-difference image which is captured by illumination light with a relatively short wavelength.
Figure 16:
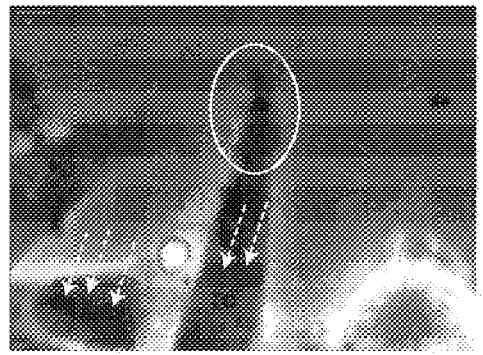
FIG. 16 is a diagram illustrating a phase-difference image which is captured by illumination light with a relatively long wavelength.

For this reason, in the stage after a week has elapsed since the seeding, it is preferable to use illumination light with a relatively long wavelength. FIG. 15 illustrates a phase-difference image which is captured by illumination light with a relatively short wavelength and FIG. 16 illustrates a phase-difference image which is captured by illumination light with a relatively long wavelength. In FIGS. 15 and 16, an arrow indicates a microstructure in the stem cell. In the cell image illustrated in FIG. 15 which is captured by illumination light with a short wavelength, the microstructure is more clearly seen than that in the cell image illustrated in FIG. 16 which is captured by illumination light with a long wavelength. In FIGS. 15 and 16, an ellipse indicates a boundary portion between the cells. As can be seen from the drawings, in the cell image illustrated in FIG. 16 which is captured by illumination light with a long wavelength, the blurring of the boundary is less than that in the cell image illustrated in FIG. 15 which is captured by illumination light with a short wavelength.

In the above-described embodiment, the method for evaluating the undifferentiation and differentiation of the stem cell has been described. However, the invention is not limited to the method for evaluating the undifferentiation and differentiation of the stem cell. For example, the degree of differentiation of a differentiation-induced cell may be evaluated or a method for evaluating, for example, the degree of malignancy of a cancer cell may be determined on the basis of the information related to maturity. The morphological characteristics of the differentiation-induced cell vary depending on the type of differentiation-induced cell. Therefore, it is preferable to set an evaluation method corresponding to a change in the morphological characteristics in advance. For example, when a cardiac muscle colony is evaluated, the distribution state of each cardiac muscle cell may be evaluated in the initial stage of culture and the pulsation cycle of the cardiac muscle cell may be evaluated in the stage in which the cardiac muscle cell is grown and starts to pulsate.

When a tissue including a blood vessel is cultured, for example, the distribution state of each cell may be evaluated in the initial stage of culture and the length or state of the blood vessel may be evaluated in the stage in which the cell is grown and the formation of the blood vessel reaches a certain level.

In addition, the cell evaluation unit 31 may acquire the information about the type of cell and may determine a cell colony evaluation method on the basis of the type of cell and the information related to maturity.

What is claimed is:
1. A cell image evaluation device comprising:
a memory; and
a processor that is connected to the memory and that is configured to:
acquire an observation image of cells captured by an imaging device;

acquire information related to maturity of the cells; and
evaluate undifferentiation and differentiation of the cells using the observation image, according to evaluation criteria of the cells corresponding to the maturity of the cells and a culture condition of the cells, wherein the information related to maturity is contained in the observation image that is a target for evaluation and the information related to maturity is a period of time from a time of seeding the cells, wherein, based on the information related to maturity, a combination of types of the evaluation criteria that is used for evaluating a differentiation or an undifferentiation of the observation image is changed, and, based on the information related to maturity, a weight that is respectively added to the plurality of the evaluation criteria that is used for evaluating the observation image is changed, and wherein, in a case in which the maturity is in an initial stage of seeding, the processor performs a process of extracting a cell colony from the observation image when the culture condition is a colony seeding method of seeding the cells by cell colony and estimates the cell colony from the cells in the observation image when the culture condition is a single cell seeding method of seeding the cells by cell.

2. The cell image evaluation device according to claim 1, wherein the evaluation criteria include an evaluation criterion based on the uniformity of a distribution of the cells and an evaluation criterion based on a shape of a colony of the cells.

3. The cell image evaluation device according to claim 1, wherein the processor is further configured to set the weights such that a weight on an outward shape of the cell colony when the maturity is equal to or greater than a predetermined value is greater than a weight on the shape of the cell colony when the maturity is less than the predetermined value.

4. The cell image evaluation device according to claim 1, wherein, when the maturity is equal to or greater than the predetermined value, the observation image is evaluated, using the uniformity of brightness of the observation image as the evaluation criteria.

5. The cell image evaluation device according to claim 1, wherein, when the maturity is equal to or greater than the predetermined value, the observation image is evaluated, using the uniformity of a thickness of the cells distributed in the observation image as the evaluation criteria.

6. The cell image evaluation device according to claim 1, wherein, when the maturity is equal to or greater than the predetermined value, the observation image is evaluated, using the approximation between a combination pattern of a plurality of circles and the cell colony as the evaluation criteria.

7. The cell image evaluation device according to claim 1, wherein the processor is further configured to change the observation image evaluation method on the basis of culture conditions of the cell.

8. The cell image evaluation device according to claim 1, wherein, when culture conditions are that a cell different from the cells is used, the processor performs a process of separating an image of the different cell from the cells.

9. A cell image evaluation method comprising:
when an observation image of cells is acquired and evaluated, acquiring information related to maturity of the cells, the information related to maturity being contained in the observation image that is a target for evaluation and the information related to maturity is a period of time from a time of seeding the cell; and determining a method for evaluating undifferentiation and differentiation of the cells using the observation image, according to evaluation criteria of the cells corresponding to the maturity of the cells and a culture condition of the cells, wherein, based on the information related to maturity, a combination of types of the evaluation criteria that is used for evaluating a differentiation or an undifferentiation of the observation image is changed, and, based on the information related to maturity, a weight that is respectively added to the plurality of the evaluation criteria that is used for evaluating the observation image is changed, wherein, in a case in which the maturity is in an initial stage of seeding, extracting a cell colony from the observation image when the culture condition is a colony seeding method of seeding the cells by cell colony and estimating the cell colony from the cells in the observation image when the culture condition is a single cell seeding method of seeding the cells by cell.

10. A non-transitory computer readable recording medium having a cell image evaluation program stored therein, that causes a computer to perform the following functions:
acquire an observation image of cells;
acquire information related to maturity of the cell; and
evaluate undifferentiation and differentiation of the cells using the observation image, according to evaluation criteria of the cells corresponding to the maturity of the cells and a culture condition of the cells, wherein the information related to maturity is contained in the observation image that is a target for evaluation and the information related to maturity is a period of time from a time of seeding the cells, wherein, based on the information related to maturity, a combination of types of the evaluation criteria that is used for evaluating a differentiation or an undifferentiation of the observation image is changed, and, based on the information related to maturity, a weight that is respectively added to the plurality of the evaluation criteria that is used for evaluating the observation image is changed, and wherein, in a case in which the maturity is in an initial stage of seeding, extracting a cell colony from the observation image when the culture condition is a colony seeding method of seeding the cells by cell colony and estimating the cell colony from the cells in the observation image when the culture condition is a single cell seeding method of seeding the cells by cell.

11. The cell image evaluation device according to claim 1, wherein based on the information related to maturity, a weight, that is respectively added to the plurality of the evaluation criteria that is used for evaluating the observation image, is changed.

* * * * *